US008771763B2

(12) United States Patent
Asiedu et al.

(10) Patent No.: US 8,771,763 B2
(45) Date of Patent: Jul. 8, 2014

(54) COMPOSITION FOR TREATING AIDS AND ASSOCIATED CONDITIONS

(71) Applicant: Wilfred-Ramix, Inc., Bridgewater, NJ (US)

(72) Inventors: William Asiedu, Accra (GH); Frederick Asiedu, Accra (GH); Manny Ennin, Accra (GH); Michael Nsiah Doudu, Accra (GH); Charles Antwi Boateng, Accra (GH); Kwasi Appiah-Kubi, Accra (GH); Seth Opoku Ware, Accra (GH); Debrah Boateng, Accra (GH); Kofi Ampim, Accra (GH); William Owusu, Accra (GH); Akwete Lex Adjei, Bridgewater, NJ (US)

(73) Assignee: Wilfred-Ramix, Inc., Bridgewater, NJ (US)

(*) Notice: Subject to any disclaimer, the term of this patent is extended or adjusted under 35 U.S.C. 154(b) by 0 days.

(21) Appl. No.: 13/949,613

(22) Filed: Jul. 24, 2013

(65) Prior Publication Data

US 2014/0023731 A1    Jan. 23, 2014

Related U.S. Application Data

(60) Division of application No. 12/828,956, filed on Jul. 1, 2010, now abandoned, which is a continuation of application No. 10/902,993, filed on Jul. 30, 2004, now Pat. No. 7,749,544, which is a continuation of application No. 10/241,973, filed on Sep. 12, 2002, now abandoned.

(51) Int. Cl.
| | | |
|---|---|---|
| A61K 36/21 | (2006.01) | |
| A61K 36/22 | (2006.01) | |
| A61K 36/86 | (2006.01) | |
| A61K 36/24 | (2006.01) | |

(52) U.S. Cl.
USPC ......................................................... 424/725

(58) Field of Classification Search
CPC ........................... A61K 36/00; A61K 2300/00
USPC .................................................. 424/725, 769
See application file for complete search history.

(56) References Cited

U.S. PATENT DOCUMENTS

| | | |
|---|---|---|
| 4,761,286 A | 8/1988 | Hiji |
| 4,923,697 A | 5/1990 | Albeck et al. |
| 4,940,726 A | 7/1990 | Pettit et al. |
| 5,227,383 A | 7/1993 | Clark et al. |
| 5,545,623 A | 8/1996 | Matsumori |
| 5,607,673 A | 3/1997 | Bashengezi |
| 5,919,460 A | 7/1999 | Ingram |
| 6,132,725 A | 10/2000 | Kadono et al. |
| 7,749,544 B2 | 7/2010 | Asiedu et al. |
| 2004/0052868 A1 | 3/2004 | Asiedu et al. |
| 2010/0266715 A1 | 10/2010 | Asiedu et al. |

FOREIGN PATENT DOCUMENTS

| | | |
|---|---|---|
| WO | 9825633 A2 | 6/1998 |
| WO | 9951249 A1 | 10/1999 |
| WO | 0016793 A1 | 3/2000 |
| WO | 0232444 A1 | 4/2002 |

OTHER PUBLICATIONS

"Alstonia—The Plant List," http://www.theplantlist.org/brows/A/Apocynaceae/Alstonia, accessed May 9, 2013, 3 pages.
"Anogeissus—The Plant List," http://www.theplantlist.org/brows/A/Combretaceae/Anogeissus, accessed May 9, 2013, 2 pages.
"Cleistopholis—The Plant List," http://www.theplantlist.org/brows/A/Annonaceae/Cleistopholis, accessed May 9, 2013, 2 pages.
"Combretum—The Plant List," http://www.theplantlist.org/brows/A/Combretacaea/Combretum, accessed May 9 2013, 13 pages.
"Dichapetalum—The Plant List," http://www.theplantlist.org/brows/A/Dichapetalaceae/Dichapetalum, accessed May 9, 2013, 7 pages.
"Gongronema—The Plant List," http://www.theplantlist.org/brows/A/Apocynaceae/Gongronema, accessed May 9, 2013, 2 pages.
"Strophanthus (plant genus)—Britannica Online Encyclopedia," http://www.britannica.com/EBchecked/topic/569535/Strophanthus, accessed May 9, 2013, 2 pages.
"Uvariastrum—The Plant List," http://www.theplantlist.org/brows/A/Annonaceae/Uvariastrum, accessed May 9, 2013, 2 pages.

(Continued)

*Primary Examiner* — Susan Hoffman
(74) *Attorney, Agent, or Firm* — Frommer Lawrence & Haug LLP; Marilyn Matthes Brogan; Kathleen N. Ehrhard

(57) ABSTRACT

An Aids and associated conditions related to Aids treating compositions is disclosed. The compositions comprise: a medicament selected from an extract of at least one of the following plant families: Apocynaceae (*Pleioscarpa Bicarpellata*); Annonaceae (*Cleistopholis Patens*); Dichapetalaceae (*Dichapetehan Madagasca Riense*); Annoceae (*Uvaristrum Pierreanum*); Cynocynaceae (*Strophantus Gratus*); Asclepiadaceae (*Gongronema Latifolium*); Combretaceae (*Combretum Racemosum*); Apocynaceae (*Alostonia Boonei*); Amaranthaceae (*Alternanthera Pungens*); Aroceae (*Anchomanes Differmis*); Cyperaceae (*Seleria Voivinil*); Anacardiaceae (*Lannea Acida*); Bignodaceae (*Kigelia Africana*); Bombacaceae (*Ceiba Pentanota*); Anarcardiaceae (*Antrocaryon Micraster*); Bombacaceae (*Bombax Bounopozense*): Anarcardiaceae (*Spondias Mombin*); Caricaceae (*Carica Papaya*); a glyceryl ester of any of the foregoing extracts; a saponin of any of the foregoing extracts; an alkaloid of any of the foregoing extracts; a protein of any of the foregoing extracts; a fat of any of the foregoing extracts; a sugar of any of the foregoing extracts; and any mixture of any of the foregoing.

2 Claims, No Drawings

(56) References Cited

OTHER PUBLICATIONS

Akah, P. A. et al., "Evaluation of Nigerian Traditional Medicines: 1. Plants Used for Rheumatic (Inflammatory) Disorders," Journal of Ethnopharmacology, vol. 42, 1994, pp. 179-182.

Atindehou, K. K. et al., "Evaluation of the Antimicrobial Potential of Medicinal Plants from the Ivory Coast," Phytotherapy Research, vol. 16, Aug. 2002, pp. 497-502.

Boyom, F. F. et al., "Aromatic plants of tropical central Africa. Part XLIII: volatile components from *Uvariastrum pierreanum* Engl. (Engl. & Diels) growing in Cameroon," Flavour and Fragrance Journal, vol. 18, 2003, pp. 296-298.

Breteler, F. J., "Novitates Gabonenses 47. Another new Dichapetalum (Dichapetalaceae) from Gabon," Adansonia, vol. 25, No. 2, 2003, pp. 223-227.

Calderón et al., "Evaluation of Diuretic Activity of *Alteranthera pungens* Extract in Rats," Phytotherapy Research, vol. 11, 1997, pp. 606-608.

Duke, J. A. et al., "Handbook of Medicinal Herbs, Second Edition," CRC Press, USA, 2002, pp. 364, "Abbreviations" section, 815-819, 821-827.

Engler, A. et al., "Die Naturlichen: Pflanzenfamilien," 1897, p. 349.

Ginsberg, et al., "Challenges in tuberculosis drug research and development," Nature Medicine, vol. 13, No. 3, Mar. 2007, pp. 290-294.

Keshinro, O. O., "The Unconventional Sources of Ascorbic Acid in the Tropics," Nutrition Reports International, vol. 31, No. 2, Feb. 1985, pp. 381-387.

Njoku, C. J. et al., "The Anthelmintic Activities of *Pleiocarpa bicarpellata* Leaf Aqueous Extract," Fitoterapia, vol. 67, No. 4, 1996, pp. 339-343.

Ojewole, J. A. O., "Studies on the Pharmacology of Echitamine, and Alkaloid from the Stem Bark of *Alstonia boonei* L. (Apocynaceae)," International Journal of Crude Drug Research, vol. 22, No. 3, 1984, pp. 121-143.

Sanogo, R. et al., "Evaluation of Malian Traditional Medicines: Screening for Antimicrobial Activity," Phytotherapy Research, vol. 12, 1998, pp. S154-S156.

Sultana, S. et al., "A Flavanone from *Lannea acida*," Phytochemistry, vol. 25, No. 4, 1986, pp. 963-964.

International Search Report for International Patent Application No. PCT/US2003/028295 mailed May 17, 2004.

International Preliminary Report on Patentability for International Patent Application No. PCT/US2003/028295 mailed Dec. 21, 2004.

US 8,771,763 B2

COMPOSITION FOR TREATING AIDS AND ASSOCIATED CONDITIONS

CROSS REFERENCE TO RELATED APPLICATIONS

The present application is a Divisional of U.S. patent application Ser. No. 12/828,956, filed Jul. 1, 2010, now abandoned, which is a Continuation of U.S. patent application Ser. No. 10/902,993, filed Jul. 30, 2004, now U.S. Pat. No. 7,749,544, issued Jul. 6, 2010, which is a Continuation of U.S. patent application Ser. No. 10/241,973, filed Sep. 12, 2002, now abandoned; all of the foregoing applications are incorporated herein by reference in their entireties.

BACKGROUND OF THE INVENTION

1. Field of the Invention

This invention relates to a composition for treating AIDS and related conditions, and more particular, to a composition comprising at least one extract of a selected plant.

2. Description of the Prior Art

Patients with illnesses that, in retrospect, were manifestations of acquired immunodeficiency syndrome (AIDS) were first described in the summer of 1981 [CDC—*Pneumocystis pneumonia*—Los Angeles. MMWR 1981, 30:250-2; CDC—*Kaposi's sarcoma and Pneumocystis pneumonia among homosexual men*—New York City and California. MMWR 1981, 30:305-8]. A case definition of AIDS for national reporting was first published in the MMWR in September 1982 [CDC—*Hepatitis B virus vaccine safety: report of an inter-agency group* MMWR 1982, 31:465-67; CDC—*Update on acquired immune deficiency syndrome (AIDS)—United States.* MMWR 1982, 31:507-14]. Since then the definition has undergone minor revisions in the list of diseases used as indicators of underlying cellular immunodeficiency [Jaffe H W, Bregman D J, Selik R M. *Acquired immune deficiency syndrome in the United States: the first 1,000 cases. J Infect Dis* 1983, 148:339-45; Jaffe H W Selik R M. *Acquired immune deficiency syndrome: is disseminated aspergillosis predictive of underlying cellular immune deficiency?*, (Reply to letter), *J Infect Dis* 1984, 149:829; Selik R M, Haverkos H W, Curran J W. *Acquired immune deficiency syndrome (AIDS) trends in the United States,* 1978-1982. *Am J Med* 1984, 76:493-500; CDC, *Update: acquired immunodeficiency syndrome (AIDS)—United States.* MMWR 1984, 32:688-91]

Since the 1982 definition was published, human T-cell lymphotropic virus type III/lymphadenopathy-associated virus (HTLV-III/LAV) has been recognized as the cause of AIDS. The clinical manifestations of (HTLV-III/LAV) infection may be directly attributable to infection with this virus or the result of secondary conditions occurring as a consequence of immune dysfunction caused by the underlying infection with (HTLV-III/LAV). The range of manifestations may include none, nonspecific signs and symptoms of illness, autoimmune and neurologic disorders, a variety of opportunistic infections, and several types of malignancy. AIDS was defined for national reporting before its etiology was known and has encompassed only certain secondary conditions that reliably reflected the presence of a sever immune dysfunction. Current laboratory tests to detect (HTLV-III/LAV) antibody make it possible to include additional serious conditions in the syndrome, as well as to further improve the specificity of the definition used for reporting cases.

The current case definition of AIDS has provided useful data on disease trends, because it is precise, consistently interpreted, and highly specific. Other manifestations of HTLV-II/LAV infections than those currently proposed to be reported are less specific and less likely to be consistently reported nationally. Milder disease associated with HTLV-III/LAV infections and asymptomatic infections may be reportable in some states and cities but will not be nationally reportable. Because persons with less specific or milder manifestations of HTLV-III/LAV infection may be important in transmitting the virus, estimates of the number of such persons are of value. These estimates can be obtained through epidemiologic studies or special surveys in specific populations.

Issues related to the case definition of AIDS were discussed by the Conference of State and Territorial Epidemiologists (CSTE) at its annual meeting in Madison, Wis., Jun. 2-5, 1985. The CSTE approved the following resolutions:

1. that the case definition of AIDS used for national reporting continue to include only the more severe manifestations of HTLV-III/LAV infection; and 2. that the Center For Disease Control (CDC) develop more inclusive definitions and classifications of HTLV-III/LAV infection for diagnosis, treatment, and prevention, as well as for epidemiologic studies and special surveys; and 3. that the following refinements be adopted in the case definition of AIDS used for national reporting:

a. In the absence of the opportunistic diseases required by the current case definition, any of the following diseases will be considered indicative of AIDS if the patient has a positive serologic or virologic test for HTLV-III/LAV:

1. disseminated histoplasmosis (not confined to lungs or lymph nodes), diagnosed by culture, histology, or antigen detection;

2. isosporiasis, causing chronic diarrhea (over 1 month), diagnosed by histology or stool microscopy;

3. bronchial or pulmonary candidiasis, diagnosed by microscopy or by presence of characteristic white plaques grossly on the bronchial mucosa (not by culture alone);

4. non-Hodgkins' lymphoma of high-grade pathologic type (diffuse, undifferentiated) and of B-cell unknown immunologic phenotype, diagnosed by biopsy;

5. histologically confirmed Kaposi's sarcoma in patients who are 60 years old or older when diagnosed.

b. In the absence of the opportunistic diseases required by the current case definition, a histologically confirmed diagnosis of chronic lymphoid interstitial pneumonitis in a child (under 13 years of age) will be considered indicative of AIDS unless test(s) for HTLV-III/LAV are negative.

c. Patients who have a lymphoreticular malignancy diagnosed more than 3 months after the diagnosis of an opportunistic disease used as a marker for AIDS will no longer be excluded as AIDS cases.

d. To increase the specificity of the case definition, patients will be excluded as AIDS cases if they have a negative result on testing for serum antibody to HTLV-III/LAV, have no other type of HTLV-III/LAV test with a positive result, and do not have a low number of T-helper lymphocytes or a low ratio of T-helper to T-suppressor lymphocytes. In the absence of test results, patients satisfying all other criteria in the definition will continue to be included. CDC will immediately adopt the above amendments to the case definition of AIDS for national reporting.

This revision in the case definition will result in the reclassification of less than 1% of cases previously reported to CDC. The number of additional new cases reportable as a result of the revision is expected to be small. Cases included under the revised definition will be distinguishable from cases included under the old definition so as to provide a consistent basis for interpretation of trends. CDC will also develop draft classifications for disease manifestations of HTLV-III/LAV infections other than AIDS, distribute these widely for comment, and publish the results. Reported by Conference of State and Territorial Epidemiologists; AIDS Br., Div of Viral Diseases, Center for Infectious Disease, CDC.

Han et al. Disclosed a process for preparing an extracted substance from a mixture of a non-fat starch from Ricini Semen and a root of *Coptis* sp for therapeutic applications of AIDS [U.S. Pat. No. 5,928,645]. The authors maintain that the extracted substance was effective in treating AIDS but provided no clinical data as to the effect of this substance in AIDS patients. In continuing work, Han et al., demonstrated significant anti-oxidant capacity of their Ricini Semen extract using a chemiluminescence assay [Hong, E. K., Kim, Y. K. Lee, W. C., Shin, H. K., and Kim, J. B.; Measurement of antioxidation activity based on chemiluminescence reaction. In Bioluminescence and Chemiluminescence (Status Report), Eds. Szalay, A. A., Kricka, L. J., and Stanley, P., John Wiley & Sons Ltd. London, England, pp. 244-246, 1993]. Antioxidant activity of Ricini Semen extract was compared with t-butylhydroxy toluene (BHT), a potent antioxidant known to people of ordinary skill in the field of the invention. The authors therefore proposed that Ricini Semen extract has anti-HIV effect although no clinical data was presented. Investigations of the Ricini Semen extract in laboratory animals by sub-cutaneous injection revealed significant tubular necrosis, glomerulonephritis, and vacuolation in livers of male and female mice, interstitial nephritis being demonstrated as well in female mice. Rats showed similar symptoms in both of the male and female. Mitosis in the liver was typically found, and extramedullary hematopoiesis in the liver and spleen also were frequently observed. Other organs were not changed compared to controls [U.S. Pat. No. 5,928,645].

Chen et al., [U.S. Pat. No. 6,077,512] disclosed a novel topical treatment method for curing black foot disease using plant extracts. The extract medicament comprised a basis part consisting of equal amounts of ground, powdered, and mixed clove, frankincense, myrrha, fhizama arisaematis, pinellia, monkshood (root) or kusnezoff monkshood (root), and tuber of bamboo-leaved orchid, and an adjuvant part consisting of equal amounts of round, powdered, and mixed borneol, powdered soy bean, borax, *coptis* root and/or *phellodendron amureause*, and *sepia aculeata*. The medicine is used in such a manner that the powdered basis part is mixed and stirred with tea water until it becomes plaster-like, and the adjuvant part is scattered in dry form onto the wound or swollen area caused by the black foot disease before the plaster-like basis part is applied to the wound or swollen area about 0.5 cm in thickness. The wound is then bandaged and the medicine is renewed once or twice a day until fresh flesh appears in the wound. Thereafter, the medicine is continuously applied but in a dry form until the wound is completely healed. The extract medicament composition taught by Chen et al., does not have any impact on AIDS itself as a systemic disease.

SUMMARY OF THE INVENTION

The present invention is related to a composition for treating AIDS and associated conditions related to AIDS. the composition comprises a medicament which is an extract of at least one plant family.

DETAILED DESCRIPTION

The present invention relates to a novel extract medicament for use in treating AIDS, an immune deficiency or immunologically compromised disease, as well as a variety of AIDS related ailments, including recurrent and persistent fever, chronic diarrhea, dermatitis, generalized lymphodenpathy, persistent cough, general pain, tuberculosis, and amenorrhea. The extract is prepared from the bark, leaf, root and stems of at least one plant from within the apocynaceae, annonaceae, dichapetalaceae, annoceae, cynocynaceae, asclepiadaceae, combretaceae, amaranthaceae, araceac, cyperaceae, anacardiaceae, bignoniaceae, bombacaceae, and caricacea plant families.

A suitable plant is selected. Preferably a mixture of at least two plants is selected. Suitable plants are selected from a family of plants including (1) apocynaceae, (2) annonaceae, (3) dichapetalaceae, (4) annoceae, (5) cynocynaceac, (6) asclepiadaceae, (7) combretaceae, (8) amaranthaceae, (9) araceae, (10) cyperaceae, (11) anacardiaceae, (12) bignoniaceae, (13) bombacaceac, (14) anarcardiaceae and caricaceae plant families.

These plants are tropical herbs that grow naturally and can be thus cultivated in tropical, savanna, grassland or lightly wooded forests of West Africa. These desert plants can also be found in other tropical regions of the world, including Asia, Asia Minor, South America, and possibly the South-Western, Western and Plains regions of the United States. The active medicaments from these plants include, but are not limited to glyceryl esters, saponins and several derivatives of alkaloids, glycosides, proteins, fats, and sugars.

The plants per se are not employed as the requisite medicament, but rather the extract of such selected plant or plants. The extraction process for the medicaments from the respective plants comprises the following:

(a) harvesting the barks, stems, leaves and roots of each plant, and cutting these into chips and chunks;

(b) washing and drying the chips and chunks under a controlled temperature condition, typically about 15° to 68° C. for about 3 days;

(c) proportionally mixing the washed and dried materials from each plant to formulate a mixture needed for each type of clinical application;

(d) grinding the resultant mixture of plant parts to a powder composition having a particle size typically ranging in size from about 100 microns to about 10,000 microns;

(e) extracting about one part of the resultant powdery mixture in about two parts of purified water under slow percolation for about 1 to about 5 hours under a temperature in the range of about 76° to about 116° C. and allowing the mixture to cool in appropriate containers under ambient temperature conditions, i.e., about 16° to about 33° C., for approximately 1 to 2 days;

(f) re-extracting the resultant mixture in a second percolation process using approximately 2 parts of purified water under slow percolation for about 1 to about 5 hours under a temperature in the range of about 76° to about 116° C. and allowing the mixture to cool in appropriate containers under ambient temperature conditions i.e., about 16° to about 33° C., for approximately 1 to 2 days;

(g) repeating the extraction process a third time using a double portion of purified water under slow percolation for about 1 to about 5 hours under a temperature in the range of about 76° to about 116° C. and allowing the mixture to cool in appropriate containers under ambient temperature conditions i.e., about 16° to about 33° C., for approximately 1 to 2 days;

(h) adding a conventional preservative system, e.g., cresols, parabens, p-chlormoetaxylenol, benzoates, alcohols, to maintain antimicrobial preservative efficacy of the mixed plant extract;

(i) mixing the extracts in a suitable container, and subjecting the resulting elute repeatedly to filtration under appropriate pressure and temperature conditions, to yield a pure, clean, preserved plant extract for human consumption;

(j) fill the resultant extract through a stainless steel strainer into appropriate containers for distribution; and (k) labeling the containers and presenting these for storage (The resultant concentrate may also be further concentrated into powder under reduced temperature/pressure conditions, e.g, by tray drying, solvent extraction, solvent exclusion, or spray drying, to result in a yellowish-brown amporphous, powder for use as an injectable or solid product such as a tablet; or by subjecting the resultant product to a filtration through a membrane filter and then a lyophilization to give powders; and then packaging the resulting mixed extracts in appropriate closure systems for clinical use.

Typically the resultant concentrated extract contains the following compounds for each plant concentrate obtained: [see L. Watson and M. J. Dallwitz (1992) onwards). The Families of Flowering Plants Descriptions, Illustrations, Identification, and Information Retrieval. Version: 14 Dec. 2000]:

| PLANT | COMPOUNDS |
|---|---|
| (1) Apocynaceae | |
| Taxonomy: Subclass Dicotyledonae; Tenuinucelli. Dahlgren's Superorder Gentianiflorae. Species 1500. Genera 164; *Acokanthera, Adenium; Aganonerion, Aganosma;* Alafia, *Allamanda, Allomarkgrafia, Allowoodsonia, Alstonia, Alyxia, Amocalyx, Ambelania, Amsonia, Ancylobotrys, Anechites, Angadenia, Anodendron, Apocynum; Arduina, Artia, Asketanthera, Aspidosperma, Baissea, Beaumontia, Bousigonia, Cabucala, Callichilia, Calocrater, Cameraria, Carissa, Carpodinus, Carruthersia, Carvalhoa, Catharanthus, Cerbera, Cerberiopsis, Chamaeclitandra, Chilocarpus, Chonemorpha, Cleghornia, Clitandra, Condylocarpon, Couma, Craspidospermum, Crioceras, Cycladenia, Cyclocotyla, Cylindropsis, Delphyodon, Dewevrella, Dictyophleba, Dipladenia, Diplorhynchus, Dyera, Ecdysanthera, Echites, Elytropus, Epigynium, Eucorymbia, Farquharia, Fernaldia, Forsteronia, Funtumia, Galactophora, Geissospermum, Gonioma, Grisseea, Hancornia, Haplophyton, Himatanthus, Holarrhena, Hunteria, Hymenolophus, Ichnocarpus, Isonema, Ixodonerium; Kamettia, Kibatalia, Kopsia, Lacmellea, Landolphia, Laubertia, Laxoplumeria, Lepinia, Lepiniopsis, Leuconotis, Lochnera, Lyonsia, Macoubea, Macropharynx, Macrosiphonia, Malouetia, Mandevilla, Mascarenhasia, Melodinus, Mesechites, Micrechtites, Microplumeria, Molongum, Mortoniella, Motandra, Mucoa, Neobracea, Neocouma, Nerium, Nouettea, Ochrosia, Odontadenia, Orthopichonia, Oncinotis, Pachypodium, Pachouria, Papuechites, Parahancornia, Parameria, Parepigynum, Parsonsia, Peltastes, Pentalinon, Petchia, Picralima, Plectaneia, Pleiocarpa, Pleioceras, Plumeria, Pottsia, Prestonia, Pycnobotrya, Quiotania, Rauwolfia, Rhabdadenia, Rhazya, Rhigospira, Rhodocalyx, Rhyncodia, Saba, Salpinctes, Schizozygia, Secondatia, Sindechites, Spongiosperma, Skytanthus, Spirolobium, Stemmadenia, Stephanostegia, Stephanostema, Stipecoma, Strempeliopsis, Strophanthus, Tabernaemontana, Tabernanthe, Temnadenia, Thenardia, Thevetia, Tintinnabularia, Trachelospermum, Urceola, Urnularia, Vahadenia, Vallariopsis, Vallaris, Vallesia, Vinca, Voacanga, Willughbeia, Woytkowskia, Wrightia, Xylinabaria, Xylinabariopsis.* | cyanogenics, alkaloids iridoids verbascosides, proanthocyanidins, cyanidins delphinidins, flavonols, kaempferols, quercetins, ellagic acid, ursolic acid, saponins/sapogenins, aluminum salts, sucrose, oligosaccharides, and sugar alcohols |
| (2) Annonaceae | |
| Taxonomy - Subclass Dicotyledonae; Crassinucelli. Dahlgren's Superorder Magnoliiflorae; Annonales. Cronquist's Subclass Magnoliidae; Magnoliales. APG (1998) basal order; Magnoliales. Species 1200. Genera 126; *Afroguatteria, Alphonsea; Ambavia, Anaxagorea, Ancana, Annickia, Annona, Anomianthus, Anonidium, Artabotrys, Asimina, Asteranthe, Balonga; Bocagea, Bocageopsis, Boutiquea, Cananga, Cardiopetalum, Chieniodendron, Cleistochlamys, Cleistopholis, Cremastosperma,* | cyanogenics, alkaloids, iridoids, proanthocyanidins, cyaniding, flavonols, quercetins, ellagic acid, sucrose, oligosaccharides |

| PLANT | COMPOUNDS |
|---|---|
| *Cyathocalyx, Cyathostemma, Cymbopetalum, Dasoclema, Dasymaschalon, Deeringothamnus, Dendrokingstonia, Dennettia, Desmopsis, Desmos, Diclinanona, Dielsiothamnus, Disepalum, Duckeanthus, Duguetia, Ellipeia, Ellipeiopsis, Enicosanthum, Ephedranthus, Exellia, Fissistigma, Fitzalania, Friesodielsia, Froesiodendron, Fusaea, Gilbertiella, Goniothalamus, Greenwayodendron, Guamia, Guatteria, Guatteriella, Guatteriopsis, Haplostichanthus, Heteropetalum, Hexalobus, Hornschuchia, Isolona, Letestudoxa, Lettowianthus, Malmea, Marsypopetalum, Meiocarpidium, Meiogyne, Melodorum, Mezzettia, Mezzettiopsis, Miliusa, Mischogyne, Mitrella, Mitrephora, Mkilua, Monanthotaxis, Monocarpia, Monocyclanthus, Monodora, Neostenanthera, Neo-uvaria, Oncodostigma, Onychopetalum, Ophrypetalum, Oreomitra, Orophea, Oxandra, Pachypodanthium, Papualthia, Petalolophus, Phaeanthus, Phoenicanthus, Piptostigma, Platymitra, Polyalthia, Polyaulax, Polyceratocarpus, Popowia, Porcelia, Pseudartabotrys, Pseudephedranthus, Pseudoxandra, Pseuduvaria, Pyramidanthe, Raimondia, Reedrollinsia, Richella, Rollinia, Ruizodendron, Sageraea, Sapranthus, Schefferomitra, Sphaerocoryne, Stelechocarpus, Stenanona, Tetrameranthus, Tetrapetalum, Toussaintia, Tridimeris, Trigynaea, Trivalvaria, Unonopsis, Uvaria, Uvariastrum, Uvariodendron, Uvariopsis, Woodiellantha, Xylopia.*<br>(3) dichapetalaceae | |
| Taxonomy. Subclass Dicotyledonae; Crassinucelli. Dahlgren's Superorder Malviflorae; Euphorbiales, Cronquist's Subclass Rosidae; Celastrales. APG (1998) Eudicot; core Eudicot; Rosid; Eurosid I; Malpighiales. Species 200. Genera 3; *Dichapetalum, Stephanopodium, Tapura,* (*Gonypetalum, Falya*)<br>(4) Annoceae | alkaloids, saponins, aluminium salts, oligosaccharides, sucrose |
| Schefferomitra subaequalis, Goniothalamus sesquipedalis<br><br>(5) Cynosuraceae | Alkaloids, cyanidins, flavonols, eg. kaempferol, quercetin, and myricetin; saponins/sapogenins sugars as sucrose; oligosaccharides or sugar alcohols |
| *Aegilopaceae, Agrostidaceae, Alopecuraceae, Andropogonaceae; Anomochloaceae, Anthoxanthaceae, Arundinaceae, Arundinellaceae, Asperellaceae, Avenaceae Bambusaceae, Chaeturaceae, Chloridaceae, Coleanthaceae Cynosuraceae, Echinariaceae: Ehrhartiaceae, Eragrostidaceae, Festucaceae, Glyceriaceae, Gramineae Hordeaceae, Lepturaceae, Maydaceae, Melicaceae, Miliaceae, Nardaceae, Oryzaceae, Panicaceae, Pappophoraceae, Paspalaceae: Parianaceae, Phalaridaceae, Pharaceae, Saccharaceae, Spartinaceae, Sporobolaceae, Stipaceae, Streptochaetaceae, Tristeginaceae, Triticaceae, Zeaceae*<br>(6) Asclepiadacea | alkaloids; arthroquinones, proanthocyanidins, cyanidins, flavonols, kaempferol, quercetin, myricetin, ellagic acid, aluminium, sucrose and oligosaccharides |
| Taxonomy. Subclass Dicotyledonae; Tenuinucelli. Dahlgren's Superorder Gentianiflorae; Gentianales. Cronquist's Subclass Asteridae; Gentianales. APG (1998) Eudicot; core Eudicot; Asterid; Euasterid I; Gentianales (as a synonym of Apocynaceae); Species 2000, Genera 250; *Absolmsia, Adelostemma, Aidomene, Amblyopetalum, Amblystigma, Anatropanthus, Anisopus, Anisotoma, Anomotassa, Araujia; Asclepias, Aspidoglossum, Astephanus, Barjonia, Belostemma, Bidaria, Biondia, Blepharodon, Blyttia, Brachystelma, Calotropis, Campestigma, Caralluma, Ceropegia, Cibirhiza, Cionura, Clemensiella, Conomitra,. Cordylogyne, Corollonema, Cosmostigma, Costantina,* | alkaloids, hydrocitric-acid, L-carnitine, 3B glucuronides of different acetylated gymmemagenins, gymnemic acid a complex mixture of at least 9 closely related acidic glucosides, flavonols including kaempferol, kaempferol and quercetin, aluminium, sucrose and oligosaccharides, iridoids. |

-continued

| PLANT | COMPOUNDS |
|---|---|
| *Cyathostelma, Cynanchum, Dactylostelma, Dalzielia, Decabelone, Decanema, Decanemopsis, Dicarpophora; Diplolepis, Diplostigma, Dischidanthus, Dischidia, Ditassa, Dittoceras, Dolichopetalum, Dolichostegia, Dorystephania, Dregea, Drepanostemma, Duvalia; Duvaliandra, Echidnopsis, Edithcolea, Emicocarpus, Emplectranthus, Eustegia, Fanninia, Fischeria, Fockea, Folotsia, Frerea, Funastrum, Genianthus, Glossonema, Glossostelma, Gomphocarpus, Gongronema, Gonioanthelma, Goniostemma, Gonolobus, Graphistemma, Gunnessia, Gymnema, Gymnemopsis, Harmandiella, Hemipogon, Heterostemma, Heynella, Hickenia, Holostemma, Hoodia, X-Hoodiopsis, Hoya, Hoyella, Huernia, Huerniopsis, Hypolobus, Ischnostemma, Jacaima, Janakia, Jobinia, Kanahia, Karimbolea, Kerbera, Labidostelma, Lagoa, Lavrania, Leichardtia, Leptadenia, Lhotzkyella, Lugonia, Lygisma, Macrodilassa; Macropetalum, Macroscepis, Mahafalia, Mahawoa, Manothrix, Margaretta, Marsdenia, Matelea, Melinia, Meresaldia, Merrillanthus, Metaplexis, Metastelma, Micholitzea, Microdactylon, Microloma, Microstelma, Miraglossum, Mitostigma, Morrenia, Nautonia, Nematostemma, Neoschumannia, Nephradenia, Notechidnopsis, Odontanthera, Odontostelma, Oncinema, Oncostemma, Ophionella, Orbea, Orbeanthus, Orbeopsis, Oreosparte, Orthanthera, Orthosia, Oxypetalum, Pachycarpus, Pachycymbium, Papuastelma, Parapodium, Pectinaria, Pentabothra, Pentacyphus, Pentarrhinum, Pentasachme, Pentastelma, Pentatropis, Peplonia, Pergularia, Periglossum, Petalostelma, Petopentia, Pherotrichis, Piaranthus, Platykeleba, Pleurostelma, Podandra, Podostelma, Prosopostelma, Pseudolithos, Ptycanthera, Pycnoneurum, Pycnorhachis, Quaqua, Quisumbingia, Raphistemma, Rhyncharrhena, Rhynchostigma, Rhyssolobium, Rhyssostelma, Rhytidocaulon, Riocreuxia, Rojasia, Sarcolobus, Sarcostemma, Schistogyne, Schistonema, Schizoglossum, Schubertia, Scyphostelma, Secamone, Secamonopsis, Seshagiria, Sisyranthus, Solenostemma, Sphaerocodon, Spirella, Stapelia, Stapelianthus, Stapeliopsis, Stathmostelma, Steleostemma, Stelmagonum, Stelmatocodon, Stenomeria, Stenostelma, Stigmatorhynchus, Strobopetalum, Stuckertia, Swynnertonia, Tassadia, Tavaresia, Telminostelma, Telosma, Tenaris, Tetracustelma, Tetraphysa, Thozetia, Toxocarpus, Treutlera, Trichocaulon, Trichosacme, Trichosandra, Tridentea, Tromotriche, Tweedia, Tylophora, Tylophoropsis, Vailia, Vincetoxicopsis, Vincetoxicum, Voharanga, Vohemaria, White-Sloanea, Widgrenia, Woodia, Xysmalobium* | |
| (7) Combretaceae | |
| Taxonomy. Subclass Dicotyledonae; Crassinucelli. Dahlgren's Superorder Myrtiflorae; Myrtales. Cronquist's Subclass Rosidae; Myrtales. APG (1998) Eudicot; core Eudicot; Rosid; Eurosid II; Myrtales. Species 600. Genera about 20; *Anogeissus, Buchenavia, Bucida, Calopyxis, Calycopteris, Combretum, Conocarpus, Dansiea, Guiera, Laguncularia, Lumnitzera, Macropteranthes, Melostemon, Pteleopsis, Quisqualis, Strephonema, Terminalia, Terminaliopsis, Thiloa* | alkaloids, arthroquinones, proanthocyanidins, cyanidins, flavonols, kaempferol; quercetin, myricetin, ellagic acid, aluminium, sucrose and oligosaccharides |
| (8) Amaranthaceae | |
| Taxonomy. Subclass Dicotyledonae; Crassinucelli. Dahlgren's Superorder Caryophylliflorae; Caryophyllales. Cronquist's Subclass Caryophyllidae; Caryophyllales. APG (1998) Eudicot; core Eudicot; neither Rosid nor Asterid; Caryophyllales. Species 850. Genera 74; *Achyranthes, Achyropsis, Aerva, Allmania, Alternanthera, Amaranthus, Arthraerua, Blutaparon,* | Cyanogenics, alkaloids, flavonols, quercetin, ellagic acid, betalains, saponins, sapogenins, oxalates |

| PLANT | COMPOUNDS |
|---|---|
| *Bosea, Brayulinea, Calicorema, Celosia, Centema, Centemopsis, Centrostachys, Chamissoa, Charpentiera, Chionothrix., Cyathula, Dasysphaera, Dasysphaera, Deeringia, Digera, Eriostylos, Froelichia, Gomphrena, Gossypianthus, Guilleminea, Hebanthe, Hemichroa (-Chenopodiaceae), Henonia, Herbstia, Hermbstaedtia, Indobanalia, Irenella, Iresine, Kyphocarpa, Lagrezia, Leucosphaera, Lithophila, Lopriorea, Marcelliopsis, Machowia, Nelsia, Neocentema, Nothosaerva, Nototrichium, Nyssanthes, Pandiaka, Pfaffia, Philoxerus, Pleuropetalum, Pleuropterantha, Polyrhabda, Pseudogomphrena, Pseudoplantago, Pseudosericocoma, Psilotrichopsis; Psilotrichum; Ptilotus, Pupalia, Quaternella, Sericocoma, Sericocomopsis, Sericorema, Sericostachys, Siamosia, Stilbanthus, Tidestromia, Trichuriella, Volkensinia, Woehleria, Xerosipho* | Rosifax, *Saltia*, |
| (9) Araceae | |
| Taxonomy. Subclass Monocotyledonae. Superorder Ariflorae; Arales. APG (1998) Monocot; non-commelinoid; Alismatales. Species 2000; Genera 106; *Aglaodorum, Aglaonema, Alloschemone, Alocasia, Ambrosina, Amorphophallus, Amydrium, Anadendrum, Anaphyllopsis, Anaphyllum, Anchomanes, Anthurium, Anubias, Aridarum, Ariopsis, Arisaema, Arisarum, Arophyton, Arum, Asterostigma, Biarum, Bognera, Bucephalandra, Caladium, Calla, Callopsis, Carlephyton, Cercestis, Chlorospatha, Colletogyne, Colocasia, Cryptocoryne, Culcasia, Cyrtosperma, Dieffenbachia, Dracontioides, Dracontium, Dracunculus, Eminium, Epipremnum, Filarum, Furtodoa, Gearum, Gonatanthus, Gonatopus, Gorgonidium, Gymnostachys, Hapaline, Helicodiceros, Heteroaridarum, Heteropsis, Holochlamys, Homalomena, Hottarum, Jasarum, Lagenandra, Lasia, Lasimorpha, Lysichiton, Mangonia, Monstera, Montrichardia*; *Nephthytis, Orontium, Pedicellarum, Peltandra, Philodendron, Phymatarum, Pinellia, Piptospatha, Pistia, Podolasia, Pothoidium, Pothos, Protarum, Pseudodracontium, Pseudohydrosme, Pycnospatha, Remusatia, Raphidophora, Rhodospatha, Sauromatum, Scaphispatha, Schismatoglottis, Scindapsus, Spathantheum, Spathicarpa, Spathiphyllum, Stenospermation, Steudnera, Stylochaeton, Symplocarpus, Synandrospadix, Syngonium, Taccarum,, Theriophonum, Typhonium, Typhonodorum, Ulearum, Urospatha, Urospathella, Xanthosoma, Zamiculcas, Zantedeschia, Zomicarpa, Zomicarpella* | Cyanogenics, cynogenic constituents tyrosine-derived, alkaloids, proanthocyanidins, cyanidin, flavonols, Kaempferol, quercetin, and quercetin |
| (10) Cyperaceae | |
| Taxonomy. Subclass Monocotyledonae. Superorder Commeliniflorae; Cyperales. APG (1998) Monocot; Commelinoid group; Poales. Species about 5000. Genera about 120; *Abildgaardia; Acriulus, Actinoschoenus, Afrotrilepis, Alinula, Androtrichum, Anosporum, Arthrostylis, Ascolepis, Ascopholis, Baeothryon, Baumea, Becquerelia, Bisboeckelera, Blysmopsis, Blysmus, Bolboschoenus, Bulbostylis, Calyptrocarya, Capitularina, Carex, Carpha, Caustis, Cephalocarpus, Chorizandra, Chrysitrix, Cladium, Coleochloa, Costularia Courtoisina, Crosslandia, Cyathochaeta, Cyathocoma, Cymophyllus, Cyperus, Desmoschoenus, Didymiandrum; Diplacrum, Diplasia, Dulichium, Egleria, Eleocharis, Eleogiton, Epischoenus, Eriophoropsis, Eriophorum, Erioscirpus, Evandra, Everardia, Exocarya, Exochogyne, Ficinia, Fimbristylis, Fuirena, Gahnia, Gymnoschoenus, Hellmuthia, Hemicarpha, Hymenochaeta, Hypolytrum, Isolepis, Kobresia, Kyllinga, Kyllingiella, Lagenocarpus, Lepidosperma, Lepironia, Lipocarpha, Lophoschoenus, Machaerina,* | Alkaloids, proanthocyanidins, cyanidins, delphinidins, flavonols, quercetins, aluminium |

| PLANT | COMPOUNDS |
|---|---|
| *Mapania, Mapaniopsi, Mariscus, Mesomelaena, Microdracoides, Micropapyrus, Monandrus, Morelotia, Neesenbeckia, Nemum, Nelmesia, Oreobolopsis, Oreobolus, Oxycaryum, Paramapania, Phylloscirpus, Pleurostachys, Principina, Pseudoschoenus, Ptilanthelium, Pycreus, Queenslandiella, Reedia, Remirea, Rhynchocladium, Rhynchospora, Rikliella, Schoenoplectus, Schoenoxiphium, Schoenoides, Schoenus, Scirpodendron, Scirpoides, Scirpus, Scleria, Sphaerocyperus, Sumatroscirpus, Syntrinema, Tetraria, Tetrariopsis, Thoracostachyum, Torulinium, Trachystylis, Trianoptiles, Trichoschoenus, Tricostularia, Trilepis, Tylocarya, Uncinia, Vesicarex, Volkiella, Websteria.* (11) Anacardiaceae | |
| Taxonomy. Subclass Dicotyledonae; Crassinucelli. Dahlgren's Superorder Rutiflorae;:Sapindales. Cronquist's Subclass Rosidae; Sapindales. APG (1998) Eudicot; core Eudicot; Rosid; Eurosid II; Sapindales, Species 600. Genera about 70; *Actinocheita, Anacardium, Androtium, Antrocaryon, Apterokarpos, Astronium, Baronia, Bonetiella, Bouea, Buchanania, Campnosperma, Cardenasiodendron, Choerospondias, Comocladia, Cotinus, Cyrtocarpa, Dracontomelon, Drimycarpus, Ebandoua, Euleria, Euroschinus, Faguetia, Fegimanra, Gluta, Haematostaphis, Haplorhus, Harpephyllum, Heeria, Holigarna, Koordersiodendron, Lannea, Laurophyllus, Lithrea, Loxopterigium, Loxostylis, Mangifera, Mauria, Melanochyla, Metopium, Micronychia, Montagueia, Mosquitoxylum, Nothopegia, Ochoterenaea, Operculicarya, Ozoroa, Pachycormus, Parishia, Pegia, Pentaspadon, Pleiogynium, Poupartia, Protorhus, Pseudoprotorhus, Pseudosmodingium, Pseudospondias, Rhodosphaera, Rhus, Schinopsis, Schinus, Sclerocarya, Semecarpus, Smodingium, Solenocarpus, Sorindeia, Spondias, Swintonia, Tapirira, Thyrsodium, Toxicodendron, Trichoscypha.* (12) Bignoniaceae | Alkaloids, iridoids, proanthocyanidins, delphinidins, cyanidins, flavonols, eg. kaempferol, quercetin, and myricetin; saponins/sapogenins sugars as sucrose, oligosaccharides or sugar alcohols |
| Taxonomy. Subclass Dicotyledonae; Tenuinucelli. Dahlgren's Superorder Lamiiflorae; Scrophulariales. Cronquist's Subclass Asteridae; Scrophulariales. APG (1998) Eudicot; core Eudicot; Asterid; Euasterid I; Lamiales. Species 650. Genera 110; *Adenocalymna, Amphilophium, Amphitecna, Anemopaegma, Argylia, Arrabidaea, Astianthus, Barnettia, Bignonia, Callichlamys, Campsidium, Campsis, Catalpa, Catophractes, Ceratophytum, Chilopsis, Clytostoma, Colea, Crescentia, Cuspidaria, Cybistax, Delostoma, Deplanchea, Digomphia, Dinklageodoxa, Distictella, Distictis, Dolichandra, Dolichandrone, Eccremocarpus, Ekmanianthe, Fernandoa, Fridericia, Gardnerodoxa, Glaziova, Godmania, Haplolophium, Haplophragma, Heterophragma, Hieris, Incarvillea, Jacaranda, Kigelia, Lamiodendron, Leucocalantha, Lundia, Macfadyena, Macranthisiphon, Manaosella, Mansoa, Markhamia, Martinella, Melloa, Memora, Millingtonia, Mussatia, Neojobertia, Neosepicaea, Newbouldia, Nyctcalos, Ophiocolea, Oroxylum, Pajanelia, Pandorea, Parabiognonia, Paragonia, Paratecoma, Parmentiera, Pauldopia; Perianthomega, Periarrabidaea, Perichlaena, Phryganocydia, Phyllarthron, Phylloctenium, Piriadacus, Pithecoctenium, Pleionotoma, Podranea, Potamoganos, Pseudocatalpa, Pyrostegia, Radermachera, Rhigozum, Rhodocolea, Roentgenia, Romeroa, Saritaea, Sparattosperma, Spathicalyx, Spathodea, Sphingiphila, Spirotecoma, Stereospermum, Stizophyllum, Tabebuia, Tanaecium, Tecoma, Tecomanthe, Tecomella, Tourrettia, Tynanthus, Urbanolophium, Xylophragma, Zeyheria.* | Alkaloids, iridoids arthroquinones, shikimic acid, verbascosides, cornosides, flavonols, quercetins, ursolic acid, saponins, sapogenins oligosaccharides, sucrose, sugar |

-continued

| PLANT | COMPOUNDS |
|---|---|
| For discussion of classificatory problems posed by *Scrophulariaceae*, impinging on *Bignoniaceae*, *Buddlejaceae*, *Callitrichaceae*, *Plantaginaceae*, *Hippuridaceae*, *Lentibulariaceae*, and *Hydrostachydaceae*, and such problem genera as *Paulownia* and *Schlegelia*, see Olmstead and Reeves (1995). | |
| (13) Bombacaceae | |
| Taxonomy. Subclass Dicotyledonae; Crassinucelli. Dahlgren's Superorder Malviflorae; Malvales. Cronquist's Subclass Dilleniidae; Malvales. APG (1998) Eudicot; core Eudicot; Rosid; Eurosid II; Malvales. Species 180. Genera 30; *Adansonia*, *Aguiaria*, *Bernoullia*, *Bombacopsis*, *Bombax*, *Catostemma*, *Cavanillesia*, *Ceiba*, *Chorisia*, *Coelostegia*, *Cullenia*, *Durio*, *Eriotheca*, *Gyranthera*, *Huberodendron*, *Kostermansia*, *Matisia*, *Neesia*, *Neobuchia*, *Ochroma*, *Pachira*, *Patinoa*, *Phragmotheca*, *Pseudobombax*, *Quararibea*, *Rhodognaphalon*, *Rhodagnaphalopsis*, *Scleronema*, *Septotheca*, *Spirotheca*, *Malvaceae*, *Bombacaceae*, *Sterculiaceae* and *Tiliaceae* | Alkaloids, proanthocyanidins, cyanidins, flavonols e.g. kaempferol and quercetin; sucrose |
| (14) Anacardiaceae | |
| Taxonomy. Subclass Dicotyledonae; Crassinucelli. Dahlgren's Superorder Rutiflorae; Sapindales. Cronquist's Subclass Rosidae; Sapindales. APG (1998) Eudicot; core Eudicot; Rosid; Eurosid II; Sapindales. Species 600. Genera about 70; *Actinocheita*, *Anacardium*, *Androtium*, *Antrocaryon*, *Apterokarpos*, *Astronium*, *Baronia*, *Bonetiella*, *Bouea*, *Buchanania*, *Campnosperma*, *Cardenasiodendron*, *Choerospondias*, *Comocladia*, *Cotinus*, *Cyrtocarpa*, *Dracontomelon*, *Drimycarpus*, *Ebandoua*, *Euleria*, *Euroschinus*, *Faguetia*, *Fegimanra*, *Gluta*, *Haematostaphis*, *Haplorhus*, *Harpephyllum*, *Heeria*, *Holigarna*, *Koordersiodendron*, *Lannea*, *Laurophyllus*, *Lithrea*, *Loxopterigium*, *Loxostylis*, *Mangifera*, *Mauria*, *Melanochyla*, *Metopium*, *Micronychia*, *Montagueia*, *Mosquitoxylum*, *Nothopegia*, *Ochoterenaea*, *Operculicarya*, *Ozoroa*, *Pachycormus*, *Parishia*, *Pegia*, *Pentaspadon*, *Pleiogynium*, *Poupartia*, *Protorhus*, *Pseudoprotorhus*, *Pseudosmodingium*, *Pseudospondias*, *Rhodosphaera*, *Rhus*, *Schinopsis*, *Schinus*, *Sclerocarya*, *Semecarpus*, *Sorindeia*, *Smodingium*, *Solenocarpus*, *Spondias*, *Swintonia*, *Tapirira*, *Thyrsodium*, *Toxicodendron*, *Trichoscypha*. | Alkaloids, arthroquinones, proanthocyanidins, delphinidin; cyanidin, flavonols, kaempferol, quercetin, myricetin, ellagic acid, saponins, sapogenins, sucrose, oligosaccharides, sugar alcohols |
| (15) Caricaceae | |
| Taxonomy. Subclass Dicotyledonae; Crassinucelli. Dahlgren's Superorder Violiflorae; Violales. Cronquist's Subclass Dilleniidae; Violales. APG (1998) Eudicot; core Eudicot; Rosid; Eurosid II; Brassicales. Species 55. Genera 4; *Carica*, *Cylicomorpha*, *Jacaratia*, *Jarilla*. | mustard-oils, alkaloids, saponins/sapogenins |

Prior to the administration to a patient an extract or a mixture of extracts are typically diluted by combination with a pharmecologically compatible solvent, e.g., ethanol or water to produce a therapeutic solution. Typically the amount or concentration of the extract or mixed extracts in the therapeutic solution ranges from 0.0001 to 10.0 weight percent of the total weight of the solution. Of course, the extract or mixture of extracts is present in a therapeutically effective amount, that is, an amount such that the extract or mixture of extracts can be administered in a therapeutically effective amount through conventional oral, nasal, aerosol, topical, intravenous, peritoneal, etc. means.

The term "amount" as used herein refers to a quantity or to a concentration, as appropriate to the context. The amount of extract(s) that constitutes a therapeutically effective amount varies according to factors such as the potency of the extract(s) the route of administration of the formulation, and the mechanical system used to administer the formulation. A therapeutically effective amount of a particular extract or mixture of extracts can be selected by those of ordinary skill in the art with due consideration of such factors. Generally a therapeutically effective amount will be from about 0.005 parts weight to about 2 parts by weight based on 100 parts by weight of the therapeutic solution, or if in solid form, e.g., tablet or capsule, 0.001 to 10 parts by weight of the weight of the tablet or capsule.

For oral administration, either solid or fluid unit dosage forms can be prepared. For preparing solid compositions such as tablets, the extract or extract mixture is mixed into formulations with conventional ingredients, such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the extract or extract mixture with an inert pharmaceutical diluent and filling the mixture into a hard gelatin capsule of appropriate size. Soft gelatin capsules are prepared by machine encapsulation of a slurry of the extract or extract mixture with an acceptable vegetable oil, light liquid petrolatum or other inert oil.

Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic extract or extract mixture is prepared in aqueous solution in a concentration of from about 1 to about 100 mg/ml. More typically, the concentration is from about 10 to about 20 mg/ml. The formulation, which is sterile, is suitable for various parenteral routes including intra-dermal, intraarticular, intra-muscular, intravascular, and subcutaneous.

In addition to the therapeutic extract or extract mixture the compositions may include, depending on the formulation desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals.

Examples of unit dosage forms are tablets, capsules, pills, powder packets, wafers, suppositories, granules, cachets, teaspoonfuls, dropperfuls, ampoules, vials, aerosols with metered discharges, segregated multiples of any of the foregoing, and other forms as herein described.

Thus, a formulation of the invention includes a therapeutic extract(s) which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration are known to those of skill. See generally Remington's Pharmaceutical Science $15^{th}$ ed., Mack Publishing Co., Easton, Pa. (1980).

Slow or extended-release delivery systems, including any of a number of biopolymers (biological-based systems), systems employing liposomes, and polymeric delivery systems, can be utilized with the extracts described herein to provide a continuous or longterm source of therapeutic compound. Such slow release systems are applicable to formulations for topical, ophthalmic, oral, and parenteral use.

Delivery of the inventive therapeutic extract or extract mixture is usually by oral administration as a solution. However, where necessary, therapy, e.g., intra-dermal, intra-articular, intramusular or intravenous, is also employed As previously indicated, the resultant medicament extract e.g., from a single plant or a mixture of any of the aforementioned plants, has been found to be effective in treating AIDS but also in treating associated conditions related to AIDS. Such associated conditions include recurrent and persistent fever, chronic diarrhea, dermatitis, generalized lymphodenpathy, persistent cough, general pain, tuberculosis, and amenorrhea.

EXAMPLES

1. About 105 patients suffering from AIDS were treated with mixtures of plant extracts, obtained as above described as approximately 10% weight percent therapeutic solutions with the following results as reported in TABLE II, below.

TABLE II

Combinations of Plant Extract Medicaments for Treatment of AIDS Related Ailments

| Stage of AIDS Disease | Typical Symptoms | Mixture of Plant Extract Used |
|---|---|---|
| Stage 1: Critically ill - non ambulatory patients - 3-6 months duration of treatment (Complete 90 to 98%) | Significant weight loss | Apocynaceae (17 weight percent) |
| | Frequent and recurrent Fever | Annonaceae (10 weight percent) |
| | Chronic Diarrhea | Dichapetalaceae (14 weight percent) |
| | Dermatitis | Annoceae (17 weight percent) |
| | Generalized Lymphodenpathy, | Cynocynaceae (21 weight percent) |
| | Cough | Asclepiadaceae (14 weight percent) |
| | General Pain | Combretaceae (7 weight percent) |

TABLE II-continued

Combinations of Plant Extract Medicaments for Treatment of AIDS Related Ailments

| Stage of AIDS Disease | Typical Symptoms | Mixture of Plant Extract Used |
|---|---|---|
| | Pneumonia<br>Kaposi's sarcoma<br>Herpes zoster<br>Tuberculosis<br>Amenorrhea | Diluted with<br>to give a 0.5 to 25 weight<br>percent extracts solution |
| Stage 2: Moderately ill - after going through stage 1 treatment program 3-6 months duration of treatment (Complete 95%) | Lack of appetite<br>Immune dysfunction | Apoocynaceae (15 weight percent)<br>Amaranthaceae (17 weight percent)<br>Aroceae (17 weight percent)<br>Cyperaceae (17 weight percent)<br>Anacardiaceae (17 weight percent)<br>bignoniaceae (17 weight percent)<br>Diluted with water to give a 0.5<br>to 25% weight percent extract<br>solution |
| Stage 3: Relatively ill but ambulatory with good vitals after stage 2 program 3-6 months duration of treatment | Restoration of immune protection | Anoceae (17 weight percent)<br>Anarcadiaceae (20 weight percent)<br>Aroceae (20 weight percent)<br>Bombacaceae (20 weight percent)<br>Caricaceae (17 weight percent)<br>Combretaceae (6 weight percent)<br>Diluted with water to give a 0.5 to 2.5<br>weight percent extract solution |
| ORAL<br>DOSAGES: Adults 3 tablespoonsfull 3 times daily<br>Pediatric: 2 teaspoonful 3 times daily | | |

II. Treatment of HIV Patients for AIDS Related Ailments

A total of 300 patients presenting moderate to advanced stages of AIDS, particularly with respect to debilitating ailments, including persistent fever, chronic diarrhea, dermatitis, generalized lymphodenapathy, persistent cough, general pain, tuberculosis and amenorrhea, were treated with an extract mixture solution of the invention. The mixture comprised Anoceae (10 to 20 weight percent), Anarcadiaceae (15-20 weight percent), Araceae (15 to 20 weight percent) Bombacaceae (20 weight percent), Caricaceae (15 to 20 weight percent), and Combretaceae (3 to 10 weight percent). The mixture was then diluted with water to give about 10 weight percent extract solution. The solution was administered to each patient at a dose of 3 tablespoons three times per day.

All treated patients in this group of studies had none of the debilitating symptoms in the time periods indicated in TABLE III, below:

TABLE III

| Symptom | Approximate Recovery Time (Average) |
|---|---|
| R/P Fever | 1 Week |
| Chronic Diarrhea | 1 Week |
| Dermatitis | 3 Weeks |
| Generalized Lymphodenpathy | 4 Weeks |
| Cough | 2 Weeks |
| General Pain | 4 Weeks |
| Tuberculosis | 12 Weeks |
| Amenorrhea | 1 Week |

We claim:

1. A composition for use in treating symptoms of AIDS patients, comprising a mixture of aqueous extracts from the following plants:
    (a) *Pleiocarpa bicarpellata, Alstonia boonei*, or a mixture thereof;
    (b) *Alternanthera pungens;*
    (c) *Anchomanes difformis;*
    (d) *Scleria boivinii;*
    (e) *Lannea acida, Antrocaryon micraster, Spondias mombin*, or a mixture thereof; and
    (f) *Kigelia africana,*
    wherein the symptoms are one or both of: lack of appetite and immune dysfunction.

2. The composition according to claim 1, wherein
    (a) *Pleiocarpa bicarpellata, Alstonia boonei*, or a mixture thereof is present in the composition in an amount of 15 weight percent;
    (b) *Alternanthera pungens* is present in the composition in an amount of 17 weight percent;
    (c) *Anchomanes difformis* is present in the composition in an amount of 17 weight percent;
    (d) *Scleria boivinii* is present in the composition in an amount of 17 weight percent;
    (e) *Lannea acida, Antrocaryon micraster, Spondias mombin*, or a mixture thereof is present in the composition in an amount of 17 weight percent; and
    (f) *Kigelia africana* is present in the composition in an amount of 17 weight percent,
    wherein the mixture of extracts is further diluted with water to give a 0.5 to 25 weight percent extracts solution.

* * * * *